United States Patent [19]
Naqui et al.

[11] Patent Number: 5,620,895
[45] Date of Patent: Apr. 15, 1997

[54] APPARATUS FOR QUANTIFICATION OF BIOLOGICAL MATERIAL IN A LIQUID SAMPLE

[75] Inventors: Ali Naqui, Falmouth; Mark W. Pierson, Saco; Thomas R. Weschler, Cape Elizabeth, all of Me.; Stephen C. Wardlaw, Old Saybrook, Conn.; Michael P. Finnerty, Auburn; Charles R. Carpenter, Scarborough, both of Me.

[73] Assignee: Idexx Laboratories, Inc., Westbrook, Me.

[21] Appl. No.: 454,071

[22] Filed: May 30, 1995

Related U.S. Application Data

[60] Division of Ser. No. 394,315, Feb. 22, 1995, which is a continuation-in-part of Ser. No. 201,110, Feb. 23, 1994, Pat. No. 5,518,892.

[51] Int. Cl.⁶ ............................................. C12M 1/40
[52] U.S. Cl. .................. 435/288.2; 435/33; 435/34; 435/39; 435/40; 435/288.1; 435/304.1; 435/304.2; 435/810; 435/975; 422/68.1; 422/102
[58] Field of Search .................. 435/33, 34, 40, 435/39, 288.1, 288.2, 304.1, 304.2, 810, 975; 422/102, 68.1; 428/34.3

[56] References Cited

U.S. PATENT DOCUMENTS

| | | | |
|---|---|---|---|
| 3,660,033 | 5/1972 | Schwartz . | |
| 3,729,947 | 5/1973 | Higuchi | 62/60 |
| 3,787,290 | 1/1974 | Kaye | 435/301 |
| 3,863,832 | 2/1975 | Gordon | 229/30 |
| 4,083,451 | 4/1978 | Hair | 206/453 |
| 4,129,483 | 12/1978 | Bochner | 435/301 |
| 4,245,043 | 1/1981 | Lund | 435/33 |
| 4,528,220 | 7/1985 | Hwo | 428/35 |
| 4,925,789 | 5/1990 | Edberg | 435/38 |
| 4,972,952 | 11/1990 | Reisender | 206/456 |
| 5,225,346 | 7/1993 | Matsumiya et al. | 435/284 |
| 5,457,054 | 10/1995 | Meisinger et al. | 436/92 |

FOREIGN PATENT DOCUMENTS

| | | |
|---|---|---|
| 2521956 | 8/1993 | France . |
| 3991793 | 1/1992 | Germany . |
| 1196374 | 6/1970 | United Kingdom . |
| WO8200279 | 2/1982 | WIPO . |
| WO9116086 | 10/1991 | WIPO . |
| WO9319199 | 3/1993 | WIPO . |

OTHER PUBLICATIONS

"Packaging Encyclopedia" 1987 pp. 64–65.
*Patent Abstracts of Japan*, vol. 16 No. 257 (C–949), Jun. 1, 1992 & JP,A,04 058880 (Nissho Corp.).

*Primary Examiner*—Esther Kepplinger
*Assistant Examiner*—Lien Tran
*Attorney, Agent, or Firm*—Lyon & Lyon

[57] ABSTRACT

An article adapted for holding a liquid sample for quantification of biological material in the liquid sample. The article includes a bag having an upper surface sheet and a lower surface sheet enclosing a volume therebetween. The bag has an upper opening through which the liquid sample can be poured into the volume in the bag. The bag also has a plurality of partitions configured to separate one or more portions of adequate sample in the bag. Also provided is a passage through which a liquid sample can be distributed throughout the volume in the bag. The bag is made of material which can be caused to form discreet non-permeable compartments for holding separate aliquots of the liquid sample.

22 Claims, 4 Drawing Sheets

APPARATUS FOR QUANTIFICATION OF BIOLOGICAL MATERIAL IN A LIQUID SAMPLE

RELATED APPLICATION

This application is a divisional application of the copending application bearing Ser. No. 08/394,315, filed Feb. 22, 1995. Application Ser. No. 08/394,315 is a continuation-in-part of the application bearing Ser. No. 08/201,110, now U.S. Pat. No. 5,518,892, filed Feb. 23, 1994. Both of these applications are incorporated by reference herein in their entirety (including drawings).

FIELD OF THE INVENTION

This invention relates to a method of quantification of biological material in a liquid sample, and to an article for holding the liquid sample during quantification.

BACKGROUND OF THE INVENTION

Many industries need to detect and quantify the concentration and level of biological material in a liquid sample. For example, the determination of bacterial concentration in water is an essential part of water quality testing. EPA regulations require that no Coliform or *Escherichia coli* can be present in potable water. The "presence/absence" format of a testing medium, such as COLILERT® or COLILERT-18™ chemical mixture (IDEXX Laboratories, ME), either of which is used as a testing medium for *Escherichia coli* and coliform bacteria, is very useful in making this determination. COLILERT® chemical mixture is based on the Defined Substrate Technology described in Edberg, "Method and Medium for use in Detecting Target Microbes In Situ in A Specimen Sample of A Possibly Contaminated Material," U.S. Pat. No. 4,925,789.

However, there are areas where the quantification, not just the detection, of bacterial concentration is important. Examples of such areas include water waste, incoming water in water purification systems, surface water, and food testing.

The classical methods of quantification of biological material are membrane filtration and the most probable number method.

In membrane filtration, the required volume of sample is filtered through a membrane of a very small pore size to non-specifically trap bacteria. The membrane is then placed on a medium which supports the growth of the target bacteria. The medium is then incubated at a specific temperature for a specific time, and any resulting colonies are counted. A drawback of membrane filtration is that a sample which contains particles other than bacteria (e.g., a waste water sample) may clog the membrane and make it unusable. Another drawback is that the membrane traps non-target bacteria.

The most probable number method is described in Recles et al., "Most Probable Number Techniques" published in "Compendium of Methods for the Microbiological Examination of Foods", 3rd ed. 1992, at pages 105–199, and in Greenberg et al., "Standard Methods For the Examination of Water and Wastewater" (8th ed. 1992). In this method, a volume of water sample is dispensed into several tubes (e.g., 10×10, 10 tubes each containing 10 ml) and bacteria in each tube allowed to grow. After incubation at a specific temperature for a specific time, the number of positive tubes is counted. The most probable number can be determined from the formula:

$$MPN/100 \text{ ml} = \frac{P \times 100}{\text{square root of } NT}$$

where p is the number of positive tubes, N is the ml sample in negative tubes, T is the ml sample in all tubes, and MPN is the most probable number. A major drawback of the method is the range of 95% confidence limits is large, when only a few tubes are used. Such confidence limits are calculated roughly as:

$$\text{Log } (MPN) \pm 1.96 \left( \frac{0.58}{\text{square root of } n} \right)$$

where n is the number of tests.

SUMMARY OF THE INVENTION

The present invention provides a simple method for more accurate quantification of the number of bacteria in a liquid sample, or for quantification of any other type of discrete, particulate biological material within a sample. Such biological materials can include fungi or other living organisms, as well as aggregates of proteins, such as enzymes, or even co-factors using reaction mixtures well known to those in the art. The invention generally makes use of a novel article which is designed to hold a liquid sample in which chemical and/or microbiological reactants are provided. For example, such chemical reactants may be a specific biological detection medium for bacteria, such as the COLILERT® or COLILERT-18™ chemical mixture discussed above, or a specific biological detection medium for enterococcus, such as ENTEROLERT™ chemical mixture. The device used is generally in the form of a modified bag. The bag is designed to accept the liquid sample to be tested, allow that sample to be distributed throughout its internal volume, and then partitioned (by any one of a number of means) into separate compartments within the bag. Generally, such compartments will allow separate chemical reactions to occur in a plurality of aliquots of the liquid to be tested. Such compartments will also prevent one aliquot of the liquid affecting the reactions in another adjacent aliquot. In a simple embodiment, the invention features a plastic bag into which is introduced a liquid sample and that liquid sample is caused to be aliquotted by simple heat sealing of the two opposing surfaces of the bag to form mini bags each containing an aliquot of the original liquid sample.

Thus, in a first aspect, the invention features an article adapted for holding a liquid sample for quantification of biological material in the liquid sample. The article includes a bag having an upper surface sheet and a lower surface sheet enclosing a volume therebetween. The bag has an upper opening through which the liquid sample can be poured into the internal volume of the bag. The bag also has a plurality of partitions configured to separate one or more portions of a liquid sample in the bag. Also provided is a passage through which a liquid sample can be distributed throughout the volume in the bag. The bag is made of material which can be caused to form discrete non-permeable compartments for holding separate aliquots of the liquid sample. While the bag may have any particular shape, it is preferred that it is formed in a generally rectangular shape with the upper opening in a narrower end portion of the bag, and of a size sufficient to allow liquid to be readily poured into the inner volume. The upper surface sheet and lower surface sheet are simply opposing surfaces of the inner portion of the bag, and may be modified as described below.

By "partition" is meant that the article is configured in such a manner that the volume of sample is separated into one or more portions. Examples of such partitions are described below. The term is not meant to require that the partitioned liquid is not in communication with other portions of the liquid in other parts of the bag.

By "passage" is meant that a means is provided within the bag to allow more ready distribution of the liquid sample throughout the bag, and among the partitions. Examples of such passages are provided below and the term is used in a broad sense.

By "discrete" is meant that the compartments formed within the bag allow separate chemical reactions to occur within those compartments without significant affect on reactions in adjacent compartments.

By "non-significant effect" is meant that under normal usage a positive sample can be readily distinguished from a negative sample despite some communication between the compartments in the bag.

By "liquid sample" is meant to include a sample which is a liquid in its natural state (such as water), or a sample which has been liquified (such as food particles).

In preferred embodiments, the bag, as stated above, is generally rectangular with an upper opening along one narrower side of the bag, and the remaining three sides sealed to prevent liquid passage through those sides. That is, the article is formed in a manner sufficient to hold the liquid sample while the discrete compartments are formed in the article during use. In one embodiment, the lower surface sheet of the bag is partitioned to form a plurality of wells which hold the sample. The lower and upper sheets are then joined and heat-sealed along the lines of the partitions, forming a plurality of compartments for holding the liquid samples, e.g., the number of compartments is between about 40 and 60 inclusive, preferably about 50, the compartments are substantially equal size, to hold an approximately 0.1 to 2 ml aliquot; and the bag is formed from a suitable material, such as polyvinylchloride.

In yet other preferred embodiments, the plurality of partitions run approximately parallel to each other in a direction from the opening to the distal end of the bag. The partitions form a plurality of passages through which a liquid sample can flow, and the partitions are of such a length that the passage is present between the opening and the partitions to facilitate distribution of liquid sample between the partitions; a further passage may be provided between the partitions and the distal end of the bag to facilitate distribution of the liquid further between the partitions; and the bag is formed from a polyethylene co-extruded with a MYLAR® plastic, such as polyethylene terephthalate (PET).

In yet other preferred embodiments, a first plurality of compartments are of one size (e.g., 2 ml) and a second plurality and/or a third plurality of compartments are provided of different sizes, e.g., of smaller size (e.g., 0.02 and 0.2 ml) than the first plurality; and the partitions are formed as wells in either one or both of the upper and lower surface sheets (as exemplified below). These embodiments have particular application for use when the concentration of the biological material to be quantified in the sample is high. The various sizes of compartments eliminate the step of diluting the sample, thereby saving time and possible error due to dilution, and increase the range of detection.

In a related aspect, the invention features a kit for use in quantification of a biological material in a liquid sample. The kit includes an article as described above and a specific biological detection medium, such as COLILERT® or COLILERT-18™ chemical mixture. In addition, in a related aspect, the invention features the article as recited above including a liquid sample after the bag is sealed to hold the liquid sample and after the compartments in the bag are formed into discrete non-communicating compartments, as discussed above.

In a further related aspect, the invention features a method for quantification of a biological material in a liquid sample. The method includes the steps of providing an article as described above and adding a testing medium to a liquid sample which is then placed within the bag. The method further includes distributing the sample within the bag, and forming a plurality of discrete non-permeable compartments in the bag so that the mixture of testing medium and sample is secured in a plurality of separate aliquots within the compartments. The method then finally involves detection of the presence or absence of the biological material in each compartment by any of the number of standard means, for example, as described below.

In preferred embodiments, the biological material to be quantified is *Escherichia coli* and coliform bacteria and a testing medium is a specific biological detection medium such as COLILERT® or COLILERT-18™ chemical mixture; the method of forming the compartments includes heat sealing the bag to form the compartments with the seals between the compartments being non-permeable for the liquid sample, testing medium, and any resulting reactant as discussed above; and the heat sealing involves applying heat to the bag for about five seconds using a heat sealing device with a temperature of about 250°–350° F. In other preferred embodiments the method includes incubating the bag at the desired temperature for a desired time to allow growth of bacteria, or reaction of any chemical entity, within the liquid sample and test medium.

Those in the art will recognize that the novel articles of this invention and methods for their use comprise, consist of, or consist essentially of those components noted above. These terms are used in their normal sense, that is, the article consists of only those named components, or may also consist essentially of other components which do not significantly effect the utility of the article, or may comprise other components not specifically noted which may be of utility in more refined aspects of the invention.

Thus, the present invention is a novel method for quantification of biological material in a liquid sample. This method provides more reliable and faster results than the traditional methods of membrane filtration and most probable number methods. The method generally includes the following steps: adding a testing medium to the sample; placing the sample in an article designed to retain the sample and allow its ready aliquoting into a number of sub-samples; distributing the sample substantially equally among a plurality of discrete non-permeable compartments in the article; sealing the compartments so that the mixture of testing medium and sample is secured within the compartments; incubating the article; and recording and analyzing the results.

The present invention also features a novel article for holding the sample during the quantification method. The article generally comprises, consists of, or consists essentially of an opening through which a liquid sample can be poured into the article; a plurality of non-permeable partitions configured and arranged to separate the liquid sample; and a passage which allows the liquid sample to be distributed substantially evenly throughout the article. The article is made of a material which can be partitioned and sealed so that the liquid sample is separated and secured into discrete non-permeable compartments.

The article and its use depend on the presence of a plurality of compartments, which can be sealed so that they are essentially non-permeable to the sample and testing medium used, and to any resulting reaction products. The number of compartments can vary, but should be sufficient for any one sample to be analyzed with the required accuracy. In the preferred embodiments, the plurality of compartments are created either by forming wells into the bag prior to the addition of the sample, and then sealing those wells into compartments after the addition of the sample, or by dividing pre-existing partitions into compartments after the addition of the sample. Other means of accomplishing this compartment creation are possible, such as by providing a rigid frame into which the sample bag is placed, and closing the frame so as to effect the sample division by pressure from the frame at a plurality of intersecting lines. Such a frame would be left in place until the sample result is read, and then it can be removed and used with another sample.

These aspects of the invention are applicable to any discretely distributed biological material, e.g., bacteria, parasites, yeast, viruses, or protein that is present at any level in a sample, provided that one or a plurality of units of the material can be detected. The choice of testing medium will depend on the biological material to be detected. The testing medium must be a medium which will detect the presence of the biological material sought to be quantified, and preferably not detect the presence of other biological material likely to be in the medium. It must also be a material which will cause some visible or otherwise sensible change, such as color change or fluorescence, if the biological material sought to be detected is present in the sample.

As noted above, the bag used in this invention may be made from any material which can be formed into non-permeable compartments such as polyethylene, co-extruded with a MYLAR® plastic, such as polyethylene terephthalate (PET). The material chosen can vary depending on the substrate or the product of any chemical reaction. For example, in the COLILERT® product, the presence of specific bacteria is indicated by the production of orthnitrophenol (ONP) and a significant amount of this product should not be able to pass through the material of the bag after heat sealing. If the reaction produces a gas then the material can be gas permeable, but liquid non-permeable, unless detection of the presence of the gas is desired.

The invention also features a novel heat sealing device which is designed to seal a bag horizontally to dispense sample into 50–100 pouches or tubes as discussed above. In order to do that, the sealing parts are provided at an angle rather than parallel to each other, so that the air will not be trapped in the bag but will be displaced. The heat sealer is essentially a toaster and the bag with the sample is placed into the heat sealer just as a slice of bread enters a toaster. Thus, unlike prior heat sealing devices, the heat sealing blades contact each other along the length of the blade at an angle greater than 0° and less than about 45°, generally the angle is between 1° and 15° and as the sealing progresses, the two blades are brought essentially parallel to one another.

In another embodiment of the heat sealing device, the device is a heated roller sealer designed to seal the article. The article is placed on a tray which moves relative to a fixed roller which applies heat at approximately 320°–370° F. for approximately 1–2 seconds to each row of partitions in the article.

In other embodiments, the heat sealing machine is provided with a plurality of heat sealing elements so that simultaneous heat sealing and thus partitioning of a sample in the articles of this invention can be achieved.

In those embodiments described above in which different sized compartments are provided, it will be evident to those in the art that such a bag has significant advantages over those with only one sized compartment. These bags allow more accurate quantification without dilution of the sample. Thus, the advantages of such a bag are that it eliminates dilution steps (thus saving time and any possible error due to dilution), and it also saves on material necessary to perform the assay.

This invention has application in other fields, such as the quantification of bacteria in food. Present methods for detecting the presence of bacteria in food use a plastic bag to which food and a buffer are added. The bag is then placed in a machine which causes the bacteria to be released. Another version of this method uses a bag with a filter lining inside, e.g, the STOMACHER® Filter bags. The food is placed inside the lining, and the bacteria is released into the outer bag. This bag can be partitioned and compartmentalized as described above. Alternatively, the desired amount of material can be taken out of the Stomacher® bag after processing and placed into one of the embodiments of the article described herein and tested as described herein.

Other features and advantages of the invention will be apparent from the following description of the preferred embodiments thereof, and from the claims.

DETAILED DESCRIPTION OF THE INVENTION

Several embodiments of the article for use in the method for quantification of biological material in a liquid sample are set forth below.

In these embodiments, the biological material to be quantified is *Escherichia coli* and coliform bacteria, and the testing medium is COLILERT® chemical mixture. The use of these embodiments to detect *Escherichia coli* and coliform bacteria and the use of COLILERT® chemical mixture is by way of example only. The invention is applicable to any biological material that it present at any level in a liquid sample (provided that one or more units of the material can be detected), and to any applicable testing medium. For example, the invention is applicable to detection of enterococcus and of total viable bacteria.

Example: 1

Figure 1:
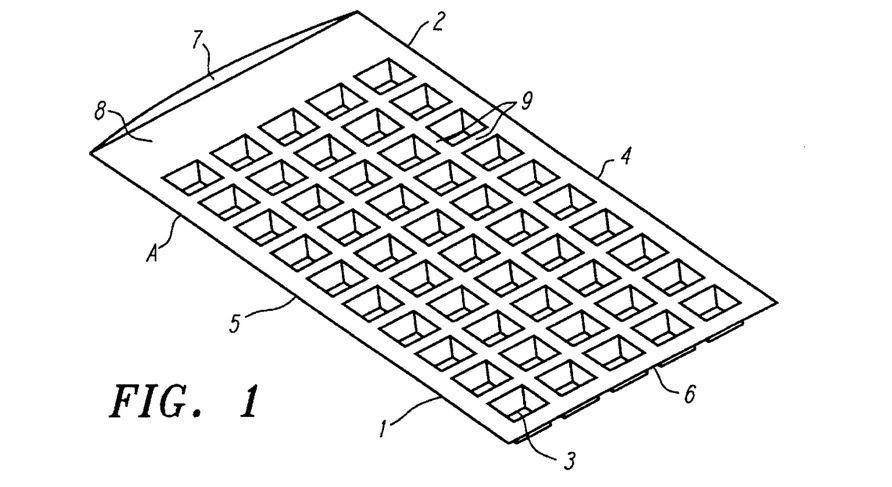
FIGS. 1, 2 and 3 are an isometric view, a top view and a side view, respectively, of an article adapted for holding liquid for use in a method for quantification of biological material in a liquid sample.
Figure 2:
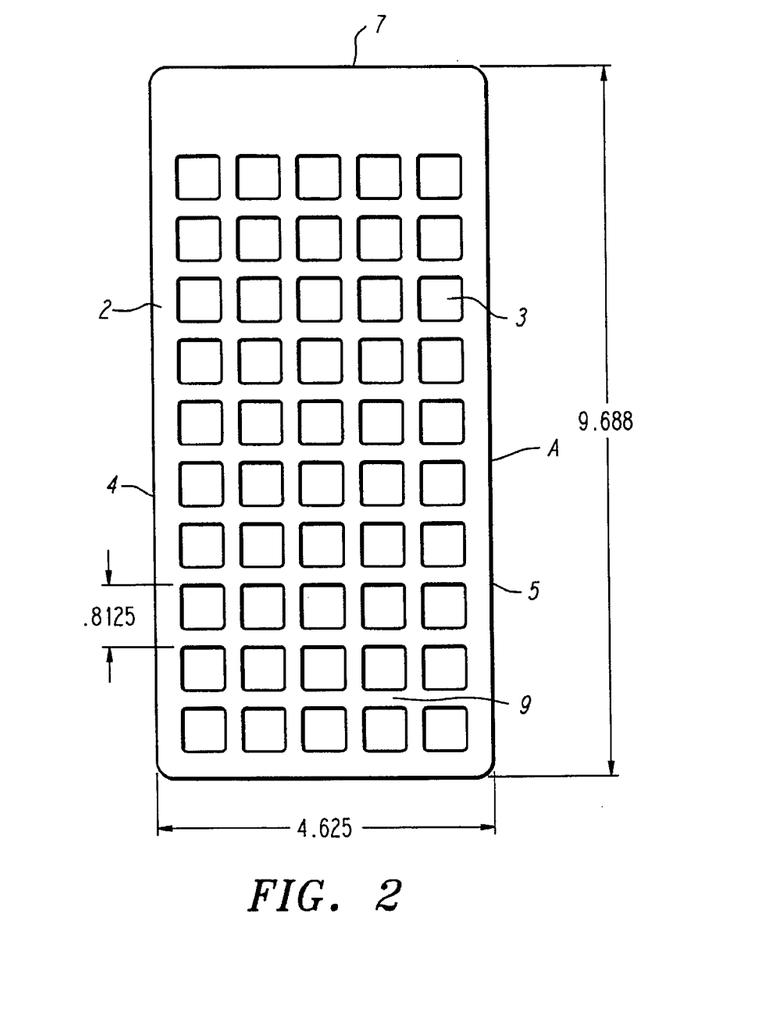
Figure 3:
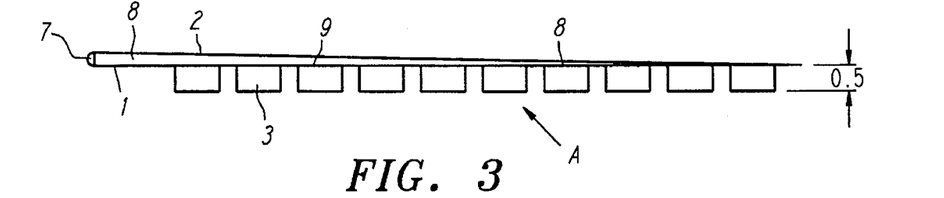

A first embodiment of the article which holds the sample during quantification is illustrated in FIGS. 1–3. Referring first to FIG. 1, Article A is shaped generally like a combination bag/ice-cube tray. Article A is formed of two generally rectangular sheets, an upper surface sheet 1 and lower surface sheet 2, made of polyvinylchloride. Upper surface sheet 1 is essentially flat.

Referring to FIGS. 1–3, lower surface sheet 2 is formed to have a number of wells 3 which protrude on one side of the sheet in a direction away from the upper surface sheet. (The dimensions of the various portions are shown in the Figures in inches.) In this embodiment, there are fifty wells 3 of equal size which each hold approximately 2 ml of liquid. Upper surface sheet 1 and lower surface sheet 2 are sealed together along the length of the two long sides 4 and 5, and along one narrow side 6. The fourth side 7 is left unsealed to create an opening through which the sample can be added to the article. Other than the three sealed sides, upper surface sheet 1 and lower surface sheet 2 are not sealed or attached, leaving a passage 8 between upper surface sheet 1 and lower surface sheet 2 which allows the sample to be distributed throughout the article and among all the wells.

Using this first embodiment, the method of quantifying the level of *Escherichia coli* and coliform bacteria in the sample is accomplished as follows. First, 100 ml of the sample to be tested and of the testing medium, the COLILERT® chemical mixture, is poured into the article through the open side 7. The mixture is dispersed substantially equally into the fifty wells 3. With 100 ml, there will be approximately 2 ml of mixture in each well 3.

The open side 7 is then sealed. Upper surface sheet 1 and lower surface sheet 2 are then sealed along vertical and horizontal partitions 9 between the wells, creating fifty discrete sealed compartments, each containing around 2 ml of sample and testing medium.

The seals can be formed by different methods, as long as the seal is non-permeable for the sample and testing medium, and any resulting reactants, and as long as the seal does not destroy or significantly harm the biological material to be quantified, or affect the testing thereof. In this embodiment, the seals are formed by heat-sealing. The heat sealing is done by applying heat to the article along the partitions for 5 seconds using a heat sealing device with a temperature of between 290° to 370° F. on the device. The resulting temperature of the liquid sample will not rise more than approximately 5°–10° F.

The article is then incubated at approximately 35° C. for approximately twenty-four hours.

The results are analyzed by counting the number of compartments which show that *Escherichia coli* and coliform bacteria is present. The presence of these organisms will be evident from a change in color of the sample. The amount of *Escherichia coli* and coliform bacteria can be determined by routine statistical analysis.

Example: 2

Referring to FIGS. 1–3 again, the heat sealing of the partitions is accomplished in a slightly different manner. A heat-activated adhesive, such as Dupont No. 5 Lid Stock Coating, is applied to the upper surface 1 in order to facilitate the sealing of upper surface 1 and lower surface 2. The heat sealing is done by applying heat to the article along the partitions for 5 seconds using a heat sealing device with a temperature of between 280° to 310° F. on the device. The advantages of this method is better sealing, and the use of a lower temperature.

Example: 3

Figure 4:
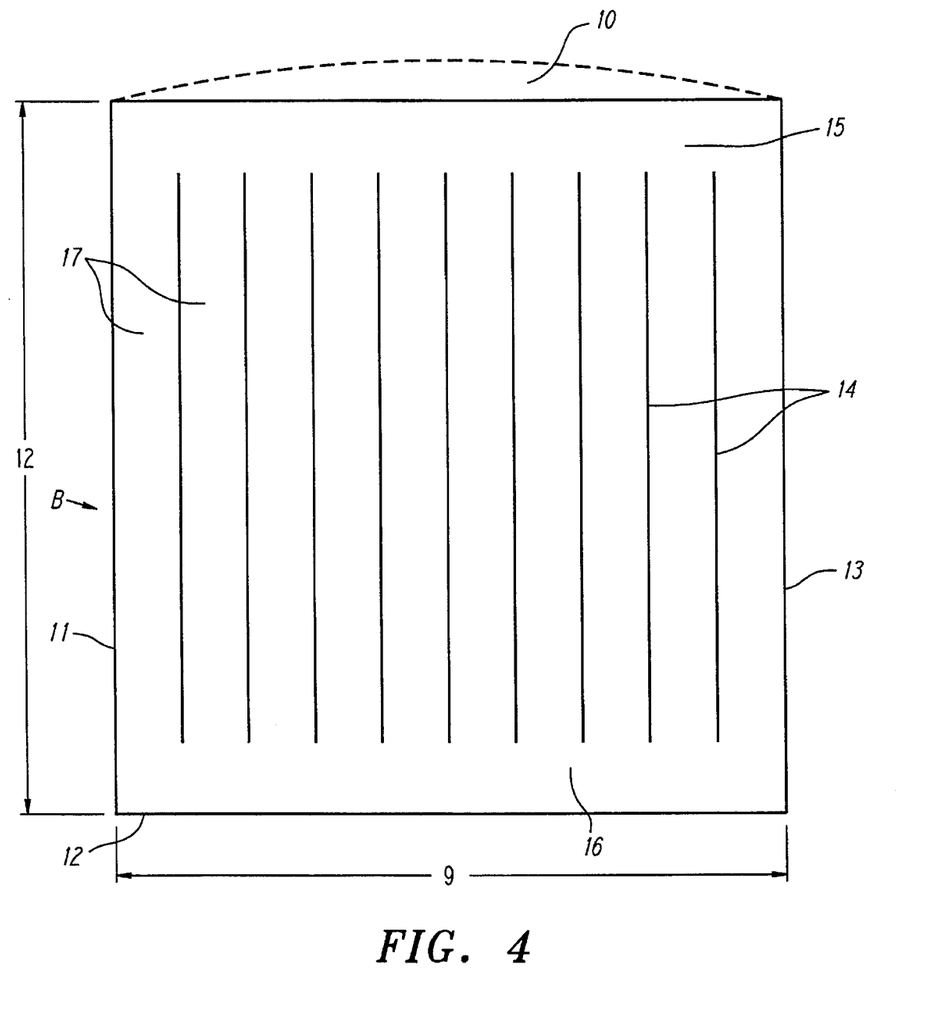
FIGS. 4 and 5 are a side view and top view respectively of another embodiment of an article useful in the invention.
Figure 5:
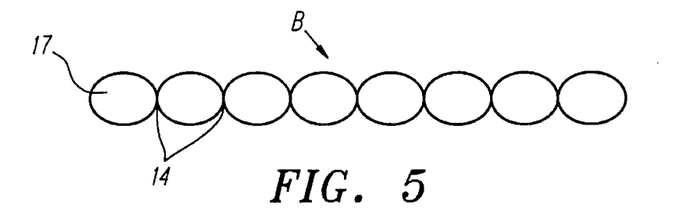

A second embodiment of the article is illustrated in FIGS. 4 and 5. Referring to FIG. 4, article B is shaped generally like a bag, with an opening 10 at the top end of the article which allows the desired quantity of sample to be poured into the article. The article is made from polyethylene (PE) co-extruded with a MYLAR® plastic, such as polyethylene terephthalate (PET). The three sides 11, 12 and 13 of the article are sealed to form a generally rectangular, bag-shaped, article.

Article B has nine vertical partitions 14 running along the length of the bag between opening 10 and an opposite end 12. Partitions 14 are also sealed. The partitions are located so that a first channel 15 is formed near the opening to facilitate pouring the sample into the article, and to insure that the sample is distributed between the partitions. A second channel 16 is left at the bottom of the article to insure that the sample moves through the article and displaces any air.

Referring to FIG. 4, a series of pre-formed passages 17 are formed between the vertical partitions 14 to insure that the sample passes between the partitions.

Using this second embodiment, the method of quantifying the level of *Escherichia coli* and coliform bacteria in the sample is accomplished as follows. First, approximately 100 ml of the sample to be tested and of the testing medium, COLILERT® chemical mixture, is poured into the article through open side 10. The mixture is dispersed throughout the article and among the partitions by way of channels 15 & 16 and passages 17. Open side 10 is then sealed. The article is then sealed along nine horizontal partitions so that these new nine partitions, along with existing partitions 14, form 100 separate compartments of approximately equal size. The sealing is performed in a manner so that the mixture of sample and testing medium is distributed substantially equally into and among these 100 compartments. There will be approximately 1 ml of sample and testing medium in each compartment.

The partitions and seals in the article can be accomplished by different methods, as long as the seal is non-permeable for the sample and testing medium, and any resulting reactants, and as long as the seal does not significantly destroy the biological material to be quantified, or affect the testing thereof. In this embodiment, the seals are done by heat-sealing. The heat sealing is done by applying heat to the article along the partitions for 2 seconds using a heat sealing wire with a temperature of around 300°–350° F.

After sealing, the article is then incubated at approximately 35° C. for approximately twenty-four hours. The results are then analyzed by counting the number of compartments which show that *Escherichia coli* and coliform bacteria is present.

Example: 4

Figure 6:
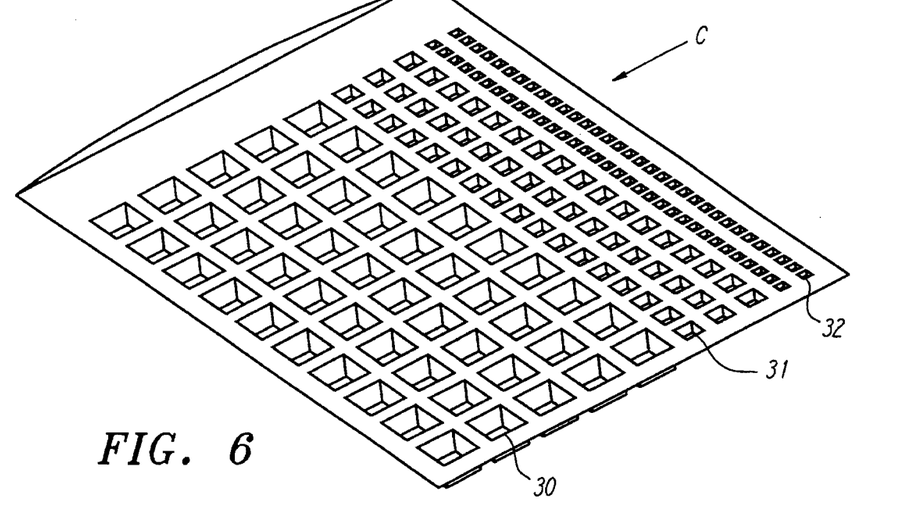
FIG. 6 is a top view of a third embodiment of an article of this invention.

A third embodiment is shown in FIG. 6, and has particular application for use when the concentration of the biological material to be quantified in the sample is high. The different sizes of compartments eliminate the step of diluting the sample, thereby saving time and possible error due to dilution. Additionally, this "autodilution" feature increases the range of the quantification.

Referring to FIG. 6, article C and its use are similar to the first embodiment described above, except that there are compartments 30, 31 and 32 of three different sizes. There are fifty compartments 30, each of which holds approximately 2 ml of sample. There are fifty compartments 31, each of which holds approximately 0.2 ml of sample. There are fifty compartments 32, each of which holds approximately 0.02 ml of sample.

Example: 5

Figure 7:
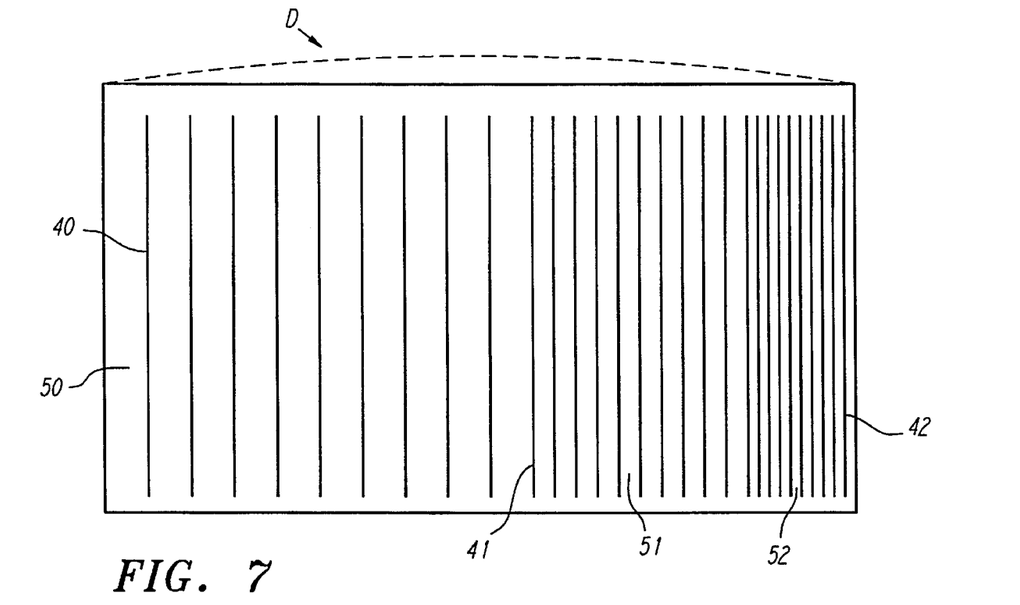
FIGS. 7 and 8 are a side view and top view respectively of a fourth embodiment of an article of this invention.
Figure 8:
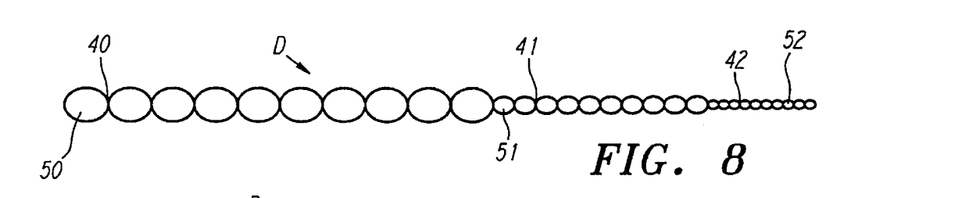

A fourth embodiment is shown in FIGS. 7 and 8, and has particular application for use when the concentration of the biological material to be quantified in the sample is high. The different sizes of compartments eliminate the step of diluting the sample, thereby saving time and possible error due to dilution, and increases the range of detection.

Referring to FIGS. 7 and 8, article D and its use are similar to the second embodiment described above, except that there are nine partitions 40 forming performed passages 50 of one size, nine partitions 41 forming performed passages 51 of a smaller size, and nine partitions 42 forming performed passages 52 of an even smaller size. The article is then sealed along nine horizontal partitions as described above in the second example. This sealing will result in 300 compartments. The new nine partitions, along with existing partitions 40, form 100 separate compartments each holding approximately 1 ml of sample. The nine new partitions, along with existing partitions 41, form 100 separate compartments each holding approximately 0.1 ml of sample. The nine new partitions, along with existing partitions 42, form 100 separate compartments each holding approximately 0.01 ml of sample.

Example: 6

Figure 9:
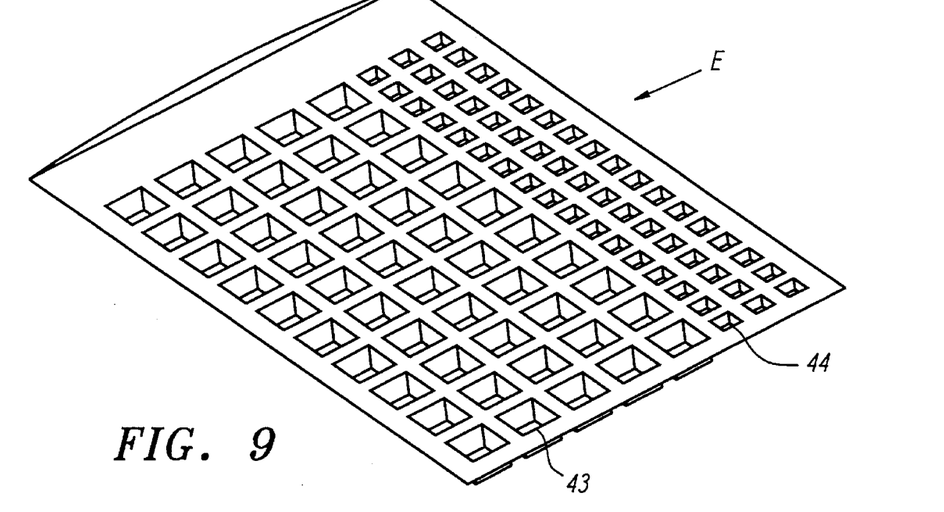
FIG. 9 is an isometric view of a fifth embodiment of an article of this invention.

A fifth embodiment is shown in FIG. 9, and has particular application for use when the concentration of the biological material to be quantified in the sample is high. The two different sizes of compartments eliminate the step of diluting the sample, thereby saving time and possible error due to the dilution. Additionally, this "autodilution" feature increases the range of the quantification.

Referring to FIG. 9, Article E and its use are similar to the third embodiment, Article C, described above, except that there are two different sizes of compartments, 43 and 44. There are fifty compartments 43, each of which holds approximately 2 ml of sample. There are fifty compartments 44, each of which holds approximately 0.2 ml of sample.

Example: 7

Figure 10:
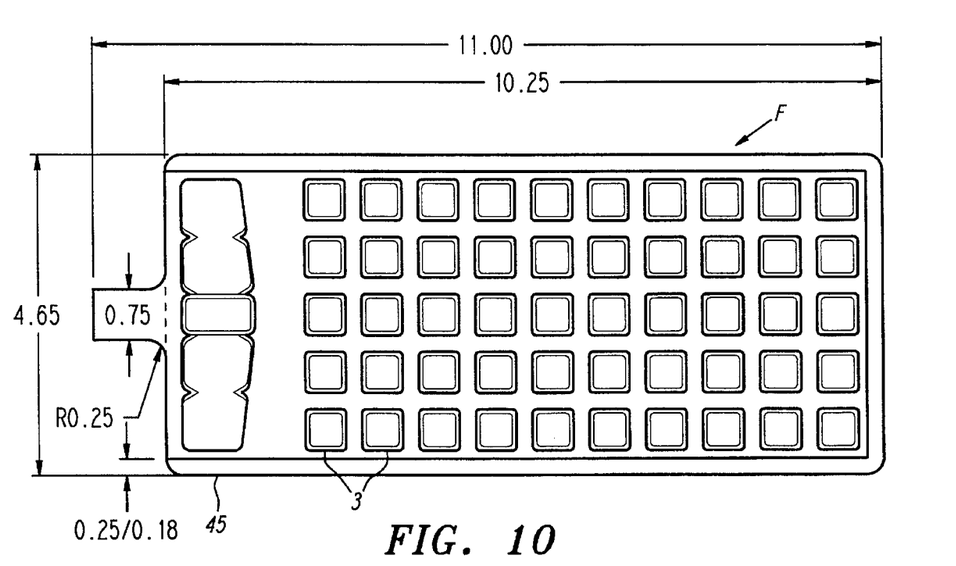
FIGS. 10 and 11 are a top view and side view, respectively, of a sixth embodiment of an article of this invention.
Figure 11:
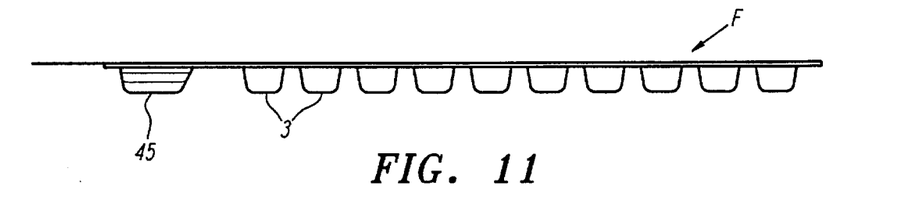

A sixth embodiment of the article, Article F, is illustrated in FIGS. 10 and 11. Referring to FIGS. 10 and 11, article F is shaped generally like Article A shown in FIGS. 1–3, with the addition of a 51st well 45. This 51st well 45 holds the overflow from the other 50 wells 3, and eliminates or reduces the risk that any liquid will overflow outside of the article during the sealing process. This well thus serves to prevent contamination of the liquid within the article.

The use of Article F is the same as for Article A, except that the results can be analyzed by counting the number of the 51 compartments, or by counting the number of the 50 compartments (excluding the 51st well), which show that *Escherichia coli* and coliform bacteria is present.

Example: 8

In a variation of the embodiment described herein, the upper surface sheet 1 is made of paper-backed foil coated with a plastic such as polyethylene and lower surface sheet 2 is made of polyvinylchloride.

Example : 9

In a smaller variation of the embodiments described herein, the article is formed to hold 10 ml in total. This variation has particular application to the food and other industries, where it is feasible or allowable to use a smaller unit of sample.

Manufacture

The above embodiments can be manufactured by standard procedures, e.g., by molding techniques well known in the art.

Use

In comparative experiments embodiments of this invention provide comparable results to traditional techniques for quantification of *Escherichia coli*. In fact, in some cases it appeared as though embodiments of this invention provided better recovery of *Escherichia coli* than other techniques.

Other embodiments are within the following claims.

What is claimed is:

1. Article adapted for holding a liquid sample for quantification of biological material in the liquid sample, comprising:

a bag having an upper surface sheet and a lower surface sheet enclosing a volume therebetween, said bag having an upper opening through which the liquid sample can be poured into said volume in said bag and said lower surface sheet comprises a plurality of preformed wells;

a plurality of partitions along said lower surface sheet in said bag which are configured to divide said plurality of wells into a plurality of discrete non-permeable compartments for holding separate aliquots of the liquid sample in said wells;

a passage through which the liquid sample can be distributed throughout the volume in the bag.

2. The article of claim 1 wherein said bag is generally rectangular, said upper opening is along one side of the bag, and the remaining three sides are sealed to prevent liquid passage therethrough.

3. The article of claim 1, wherein said compartments are formed by heat-sealing a plurality of lines along said upper and lower surface sheets of said bag.

4. The article of claim 1, wherein the number of wells is between 40 and 60 inclusive.

5. The article of claim 1, wherein the wells are of substantially equal size.

6. The article of claim 1, wherein the wells are of a size to hold approximately two ml of liquid.

7. The article of claim 1, wherein the wells are of a size to hold approximately 0.2 ml of liquid.

8. The article of claim 1, wherein the bag is formed from polyvinylchloride.

9. The article of claim 1, wherein the upper surface sheet of the bag is formed from paper-backed foil coated with polyethylene and the lower surface sheet is formed from polyvinylchloride.

10. The article of claim 1, said bag having a distal end opposite said upper opening, wherein the plurality of partitions run parallel to each other in the direction from said opening to the distal end of the bag;

wherein said partitions form a plurality of passages through which the liquid sample can flow; and wherein such partitions are of a length that said passage is present between said opening and said partitions to facilitate the distribution of the liquid sample between the partitions.

11. The article of claim 10, further comprising a second passage between the partitions and the end of the article distal to said opening to facilitate the distribution of a liquid sample between the partitions.

12. The article of claim 10, wherein said partitions are formed by heat-sealing a plurality of lines along said upper and lower surfaces of said bag.

13. The article of claim 1, wherein the bag is formed of polyethylene co-extruded with polyethylene terephthalate.

14. The article of claim 1, wherein a first plurality of the wells are of one size, and a second plurality of the wells are of a smaller size.

15. The article of claim 14 wherein a third plurality of the wells of a size different from said first and second plurality of wells.

16. A kit for use in the quantification of biological material in a liquid sample, comprising:

an article as recited in claim 1; and a specific biological detection medium.

17. The kit of claim 16, further comprising:

a heat-activated adhesive applied to the inner surface of one or both said upper and lower surface sheets.

18. Article adapted for holding a liquid sample for quantification of biological material in the liquid sample when the concentration of biological material is high, comprising:

a bag having an upper surface sheet and a lower surface sheet enclosing a volume therebetween, said bag having an upper opening through which the liquid sample can be poured into said volume in said bag;

a plurality of partitions in said bag configured to form a plurality of discrete wells in the bag for holding the liquid sample, wherein a first plurality of the wells are of one size and a second plurality of the wells are of a smaller size;

a passage through which the liquid sample can be distributed throughout the volume in the bag; and wherein the bag is made of a material which can be caused to form discrete non-permeable compartments for holding separate aliquots of the liquid sample.

19. The article of claim 18, further comprising:

a third plurality of the wells of a third size different from said first and second plurality of wells.

20. The article of claim 18, wherein said compartments are formed by heat-sealing a plurality of lines along said upper and lower surface sheets of said bag.

21. The article of claim 18, wherein:

the number of the first plurality of wells is between 40 and 60; and the number of the second plurality of wells is between 40 and 60.

22. The article of claim 18, wherein:

the first plurality of wells are of a size to hold approximately two ml of liquid; and the second plurality of wells are of a size to hold approximately 0.2 ml of liquid.

* * * * *